United States Patent [19]

Bolorforosh et al.

[11] Patent Number: 6,132,377

[45] Date of Patent: Oct. 17, 2000

[54] MEDICAL DIAGNOSTIC ULTRASONIC IMAGING SYSTEM AND METHOD USING DIFFERENTIAL SUB-BAND DETECTION TECHNIQUES

[75] Inventors: Mirsaid S. Bolorforosh, Palo Alto; Edward A. Gardner, San Jose; Gregory L. Holley, Mountain View; Ting Lan Ji, San Jose; Sriram Krishnan, San Jose; Bhaskar S. Ramamurthy, San Jose, all of Calif.

[73] Assignee: Acuson Corporation, Mountain View, Calif.

[21] Appl. No.: 09/282,402

[22] Filed: Mar. 31, 1999

[51] Int. Cl.[7] ........................................ A61B 8/00
[52] U.S. Cl. ............................. 600/458; 73/631
[58] Field of Search ...................... 600/441, 443, 600/447, 458; 73/631

[56] References Cited

U.S. PATENT DOCUMENTS

| | | | |
|---|---|---|---|
| 5,255,683 | 10/1993 | Monaghan | 600/458 |
| 5,410,516 | 4/1995 | Uhlendorf . | |
| 5,456,257 | 10/1995 | Johnson . | |
| 5,526,816 | 6/1996 | Arditi | 600/458 |
| 5,632,277 | 5/1997 | Chapman . | |
| 5,706,819 | 1/1998 | Hwang . | |
| 5,724,976 | 3/1998 | Mine . | |
| 5,733,527 | 3/1998 | Schutt . | |
| 5,740,128 | 4/1998 | Hossack et al. . | |
| 5,833,613 | 11/1998 | Averkiou . | |
| 5,961,464 | 10/1999 | Poland | 600/458 |

OTHER PUBLICATIONS

"Simulated Capillary Blood Measurement Using a Nonlinear Ultrasonic Contrast Agent," Schrope et al.; Ultrasonic Imaging, vol. 14, pp. 134–158, 1992.

"Harmonic Power Mode Doppler Using Microbubble Contrast Agents: An Improved Method for Small Vessel Flow Imaging," Burns et al., 1994 IEEE Ultrasonic Symposium, pp. 1547–1550, 1994.

"Pulse Inversion Doppler: A New Method for Detecting Nonlinear Echoes from Microbubble Contrast Agents," Simpson and Burns, 1997 IEEE Ultrasonic Symposium, 1997.

*Primary Examiner*—Francis J. Jaworski
*Attorney, Agent, or Firm*—Brinks Hofer Gilson & Lione

[57] ABSTRACT

A medical diagnostic ultrasound imaging system and method modulate the image signal as a function of the ratio of the harmonic receive signal to the fundamental receive signal. Tissue harmonic backscatter differs substantially in spectral shape as compared to contrast agent backscatter, and this method allows improved discrimination between contrast agent and tissue backscatter.

32 Claims, 4 Drawing Sheets

1

MEDICAL DIAGNOSTIC ULTRASONIC IMAGING SYSTEM AND METHOD USING DIFFERENTIAL SUB-BAND DETECTION TECHNIQUES

BACKGROUND

This invention relates to medical diagnostic ultrasound imaging, and in particular to methods and systems for distinguishing contrast agent from surrounding tissue.

Contrast agent imaging is an important medical diagnostic ultrasound imaging mode. One limitation in many contrast imaging systems is the difficulty of distinguishing echo signals from contrast agents from echo signals from surrounding tissue. This is because both contrast agents and tissue generate nonlinear return signals at frequencies other than the frequency of the insonifying signals. It is well recognized that nonlinear signals from tissue are generated by nonlinear propagation of the insonifying ultrasound wave.

Prior-art harmonic imaging methods that exploit nonlinear behaviour of contrast agent include B-mode harmonic imaging, B-mode harmonic pulse inversion imaging, harmonic power Doppler imaging, and color harmonic pulse inversion imaging.

In B-mode harmonic imaging, the signal is transmitted at a fundamental frequency f, and the receive signal is filtered to emphasize frequency components near the second harmonic, 2f. Contrast agents are known to have a stronger second harmonic response than tissue, and for this reason the receive signal from contrast agent is enhanced over that from tissue. This method is currently used by most major manufacturers of ultrasound imaging equipment. Specific examples are described in Mine U.S. Pat. No. 5,724,976, Uhlendorf U.S. Pat. No. 5,410,516, Schutt U.S. Pat. No. 5,733,527, and "Simulated Capillary Blood Measurement Using a Nonlinear Ultrasonic Contrast Agent," Schrope et al.; Ultrasonic Imaging, Vol. 14, pp. 134–158, 1992.

In B-mode harmonic pulse inversion imaging, two pulses are transmitted along the same ultrasound line, where one pulse is shifted by 180° with respect to the other. Receive signals from the two pulses are then summed, and the resultant signal is displayed. The pulse inversion technique cancels stationary fundamental frequency signals and retains second harmonic signals as well as some nonstationary fundamental signals. Examples of such methods include Chapman U.S. Pat. No. 5,632,277 and Hwang U.S. Pat. No. 5,706,819.

In harmonic power Doppler imaging, multiple pulses are transmitted along the same ultrasound line, and the receive signal is filtered about the second harmonic frequency. The resultant signals are then filtered with a high-pass filter to remove stationary signals. Examples of such methods are described in Averkiou U.S. Pat. No. 5,833,613, Johnson U.S. Pat. No. 5,456,257, and "Harmonic Power Mode Doppler Using Microbubble Contrast Agents: An Improved Method for Small Vessel Flow Imaging," Burns, et al., 1994 IEEE Ultrasonic Symposium, pp. 1547–1550, 1994.

In color harmonic pulse inversion imaging, the approach used is similar to that used in harmonic power Doppler imaging described above, but alternate pulses are shifted in phase by 180°. Such methods are described in "Pulse Inversion Doppler: A New Method for Detecting Nonlinear Echoes from Microbubble Contrast Agents," Simpson and Burns, 1997 IEEE Ultrasonic Symposium, 1997.

Though these techniques succeed in presenting contrast agent enhanced images, they do not entirely meet the needs of clinicians in the field. B-mode harmonic imaging does not differentiate between second harmonic signals generated by nonlinear propagation through tissue and second harmonic signals generated by contrast agents. Pulse inversion imaging further enhances second harmonic signals, but it still does not differentiate between second harmonic signals generated by nonlinear propagation through tissue and second harmonic signals generated by contrast agents. Harmonic power Doppler imaging attempts to differentiate contrast agent from tissue by looking for a loss of correlation between successive pulses due to agent destruction, agent motion or other methods. However, tissue motion will also result in a loss of correlation and may appear as a displayed signal. Tissue motion is reduced currently by a combination of increasing the pulse repetition frequency and/or the use of more aggressive clutter filters. However, increasing the pulse repetition frequency may reduce the signal from destroyed contrast agent, and more aggressive clutter filters may filter out contrast signal as well as tissue signal. These problems and drawbacks apply also to color harmonic pulse inversion techniques.

It would be advantageous to improve the specificity for imaging contrast agent as opposed to tissue. Increased specificity would allow contrast agent to be used for sensitive qualitative and quantitative measurements of blood flow in tissue.

SUMMARY

The present inventors have discovered specific spectral properties of the backscattered fundamental and harmonic receive signals that can be used to distinguish contrast agent from tissue in a medical diagnostic ultrasound imaging system. One preferred embodiment described below uses the ratio of the energy in the harmonic sub-band of the receive signal to the energy in the fundamental sub-band of the receive signal to detect the presence or absence of contrast agent. This ratio is then used to modulate the image signal to enhance the display of contrast agent.

The foregoing introductory paragraph is intended to present one aspect of the preferred embodiment described below by way of introduction. Nothing in this paragraph should be taken as a limitation on the following claims.

DETAILED DESCRIPTION OF THE PREFERRED EMBODIMENTS

General Discussion

Though both contrast agent and tissue produce harmonic signals in response to fundamental transmit signals, the level of the harmonic signal with respect to the fundamental signal in the backscattered receive signal is significantly different for contrast agent as compared to tissue. In the preferred embodiments that follow, this property is used to discriminate between contrast agent and tissue.

Figure 1:
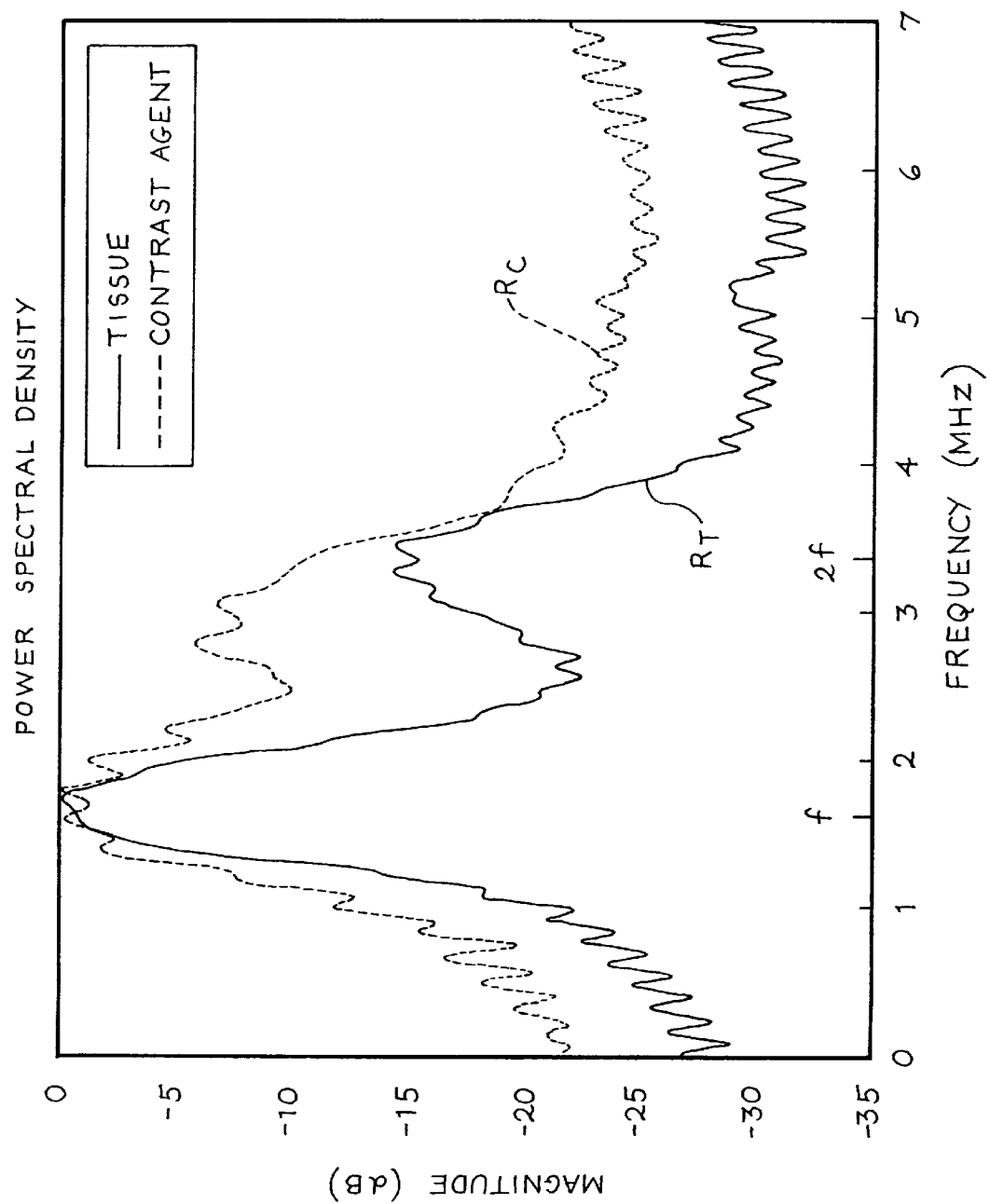
FIG. 1 is a frequency versus magnitude plot of receive signals associated with tissue and contrast agent.

FIG. 1 shows a receive signal $R_T$ associated with backscattered signals from tissue insonified at a transmit center frequency f. In $R_T$ the fundamental frequency f is 1.7 MHz and the harmonic frequency 2f is 3.4 MHz. Note that the receive signal $R_T$ peaks at the fundamental frequency f and has a magnitude at the harmonic frequency 2f that is suppressed by about 15 dB as compared to the magnitude at the fundamental frequency f.

FIG. 1 also shows a frequency versus magnitude plot of a receive signal $R_C$ associated with backscattered echo signals from contrast agent. As before, the receive signal $R_C$ is generated with a transmit signal centered at a fundamental frequency f of 1.7 MHz. The receive signal $R_C$ also shows a peak magnitude at about the fundamental frequency f, and this peak magnitude is approximately 10 dB greater than the magnitude at the harmonic frequency 2f.

FIG. 1 shows that the ratio of amplitude near the fundamental frequency f to magnitude near the harmonic frequency 2f is substantially different for echo signals from tissue and contrast agent. As explained below, this ratio can be used to discriminate echo signals from tissue versus echo signals from contrast agent.

Specific Embodiments

Figure 2:
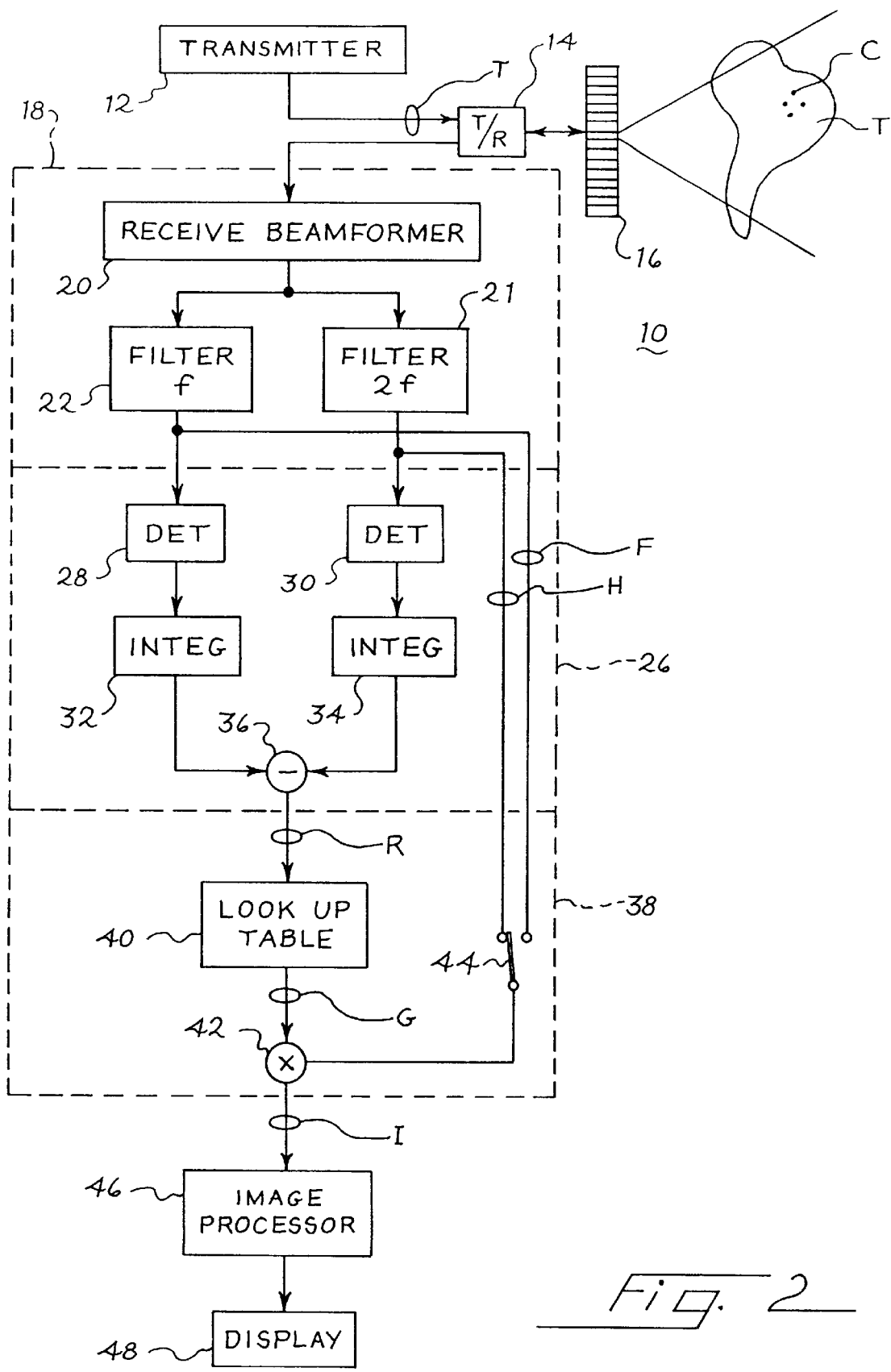
FIG. 2 is a block diagram showing a medical diagnostic ultrasound imaging system that incorporates a presently preferred embodiment to this invention.

Turning now to FIG. 2, an ultrasonic imaging system 10 includes a transmitter 12 that generates transmit signals T. The transmit signals T are applied via a transmit/receive switch 14 to a transducer probe 16. The transducer probe 16 responds to the transmit signals T by generating ultrasonic energy at the frequency of the transmit signal T and directing this ultrasonic energy into an imaged region that includes tissue T and contrast agent C.

The tissue T and the contrast agent C backscatter ultrasonic energy from the imaged region to the transducer probe 16. This backscattered ultrasonic energy causes the transducer probe 16 to generate receive signals $R_C$ and $R_T$ that are applied via the transmit/receive switch 14 to a receiver 18.

In this embodiment, the receiver 18 includes a receive beamformer 20 and two filters 22, 24. The first filter 22 is a bandpass filter that passes a sub-band of the receive signals centered around the fundamental frequency f. As before, the transmit signals T are also centered around the fundamental frequency f. The second filter 24 is another bandpass filter having a bandpass centered around the harmonic frequency 2f. The output signals generated by the filters 22, 24 are fundamental receive signals F and harmonic receive signals H, respectively.

The fundamental and harmonic receive signals F, H are applied to a ratio former 26 that in this embodiment includes first and second detectors 28, 30. The detectors 28, 30 preferably square the respective input signals and take the log of the squared result. The detected output signals generated by the detectors 28, 30 are applied to integrators 32, 34 that integrate the detected output signals over frequency. The output signals generated by the integrators 32, 34 are then subtracted from one another in a subtraction circuit 36 that in this application performs a division function. In this embodiment, the output signals of the integrators 32, 34 vary as the logarithm of the fundamental and harmonic receive signals, after detection and integration. Thus, the difference between the output signals of the integrators 32, 34 creates a ratio signal R that varies as a function of the ratio of the detected, integrated fundamental and harmonic receive signals F, H.

The ratio signal R is applied to an image signal generator 38 that in this embodiment includes a lookup table 40. The lookup table 40 generates a gain signal G in response to the ratio signal R, and this gain signal G is applied to a multiplier 42. The multiplier 42 is also responsive to one of the fundamental and harmonic receive signals F, H, as determined by the state of a switch 44. The output of the multiplier 42 is an image signal I that is applied to an image processor 46. The output of the image processor 46 is applied to a display 48.

Figure 3:
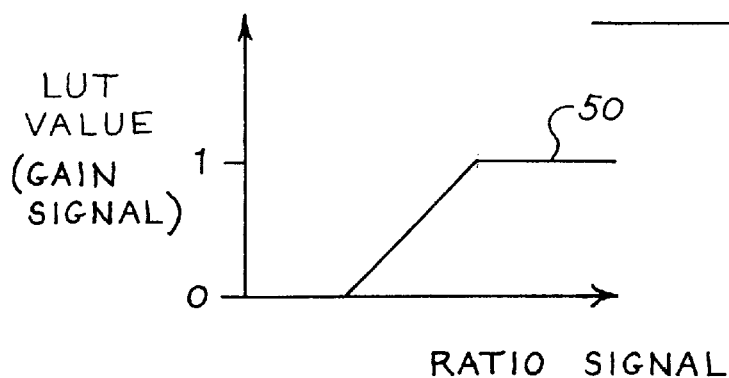
FIG. 3 is a graph showing one example of the manner in which the gain signal can vary as a function of the ratio signal in the system of FIG. 3.

The lookup table 40 allows the gain applied to the fundamental or harmonic receive signal F, H to be varied as a linear or nonlinear function of the ratio signal R. FIG. 3 shows one example of the manner in which the gain signal G can vary from a value equal to zero for low values of the ratio signal R to a value equal to one for high values of the ratio signal R. Other functions can be used in the lookup table.

Figure 4:
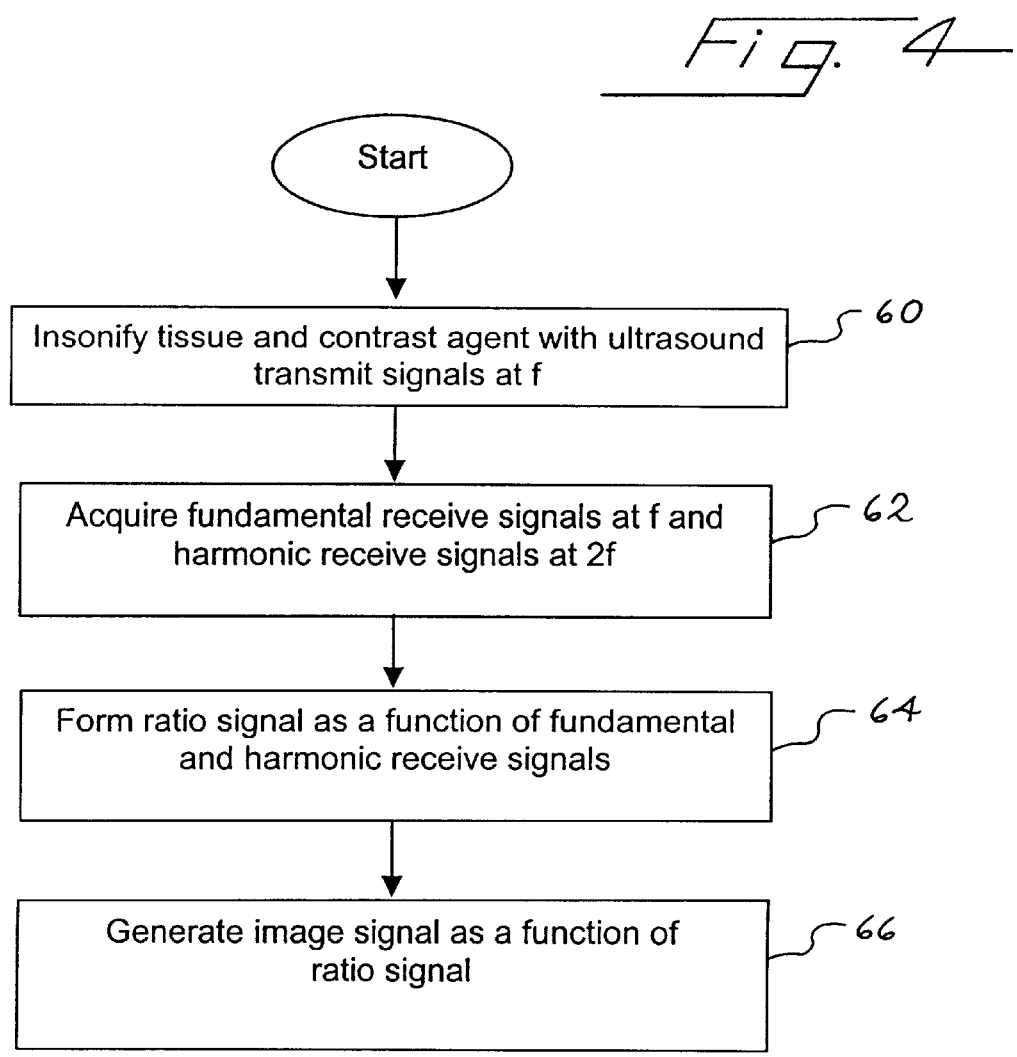
FIG. 4 is a flow chart of a preferred embodiment of the method of this invention, as practiced by the system of FIG. 1.

FIG. 4 provides a flowchart for a method practiced by the system 10 of FIG. 1. In step 60, tissue and contrast agent are insonified with ultrasound transmit signals centered at the fundamental frequency f. In step 62, fundamental receive signals centered at the fundamental frequency f and harmonic receive signals centered at the harmonic frequency 2f are acquired. In step 64, the ratio signal R is formed as a function of the fundamental and harmonic receive signals. In step 66, the image signal I is generated as a function of the ratio signal R.

As described above, regions with high concentration of contrast agent will have a relatively smaller difference between the integrated fundamental and harmonic receive signals F, H, while the regions with a small concentration of contrast agent will have a larger difference between the integrated backscattered signal levels in these two bandpass. By modulating either the fundamental or harmonic receive signal with a gain signal that varies as a function of this ratio, the image signal I can be made more specific for contrast agent or for tissue harmonics, as desired.

Figure 5:
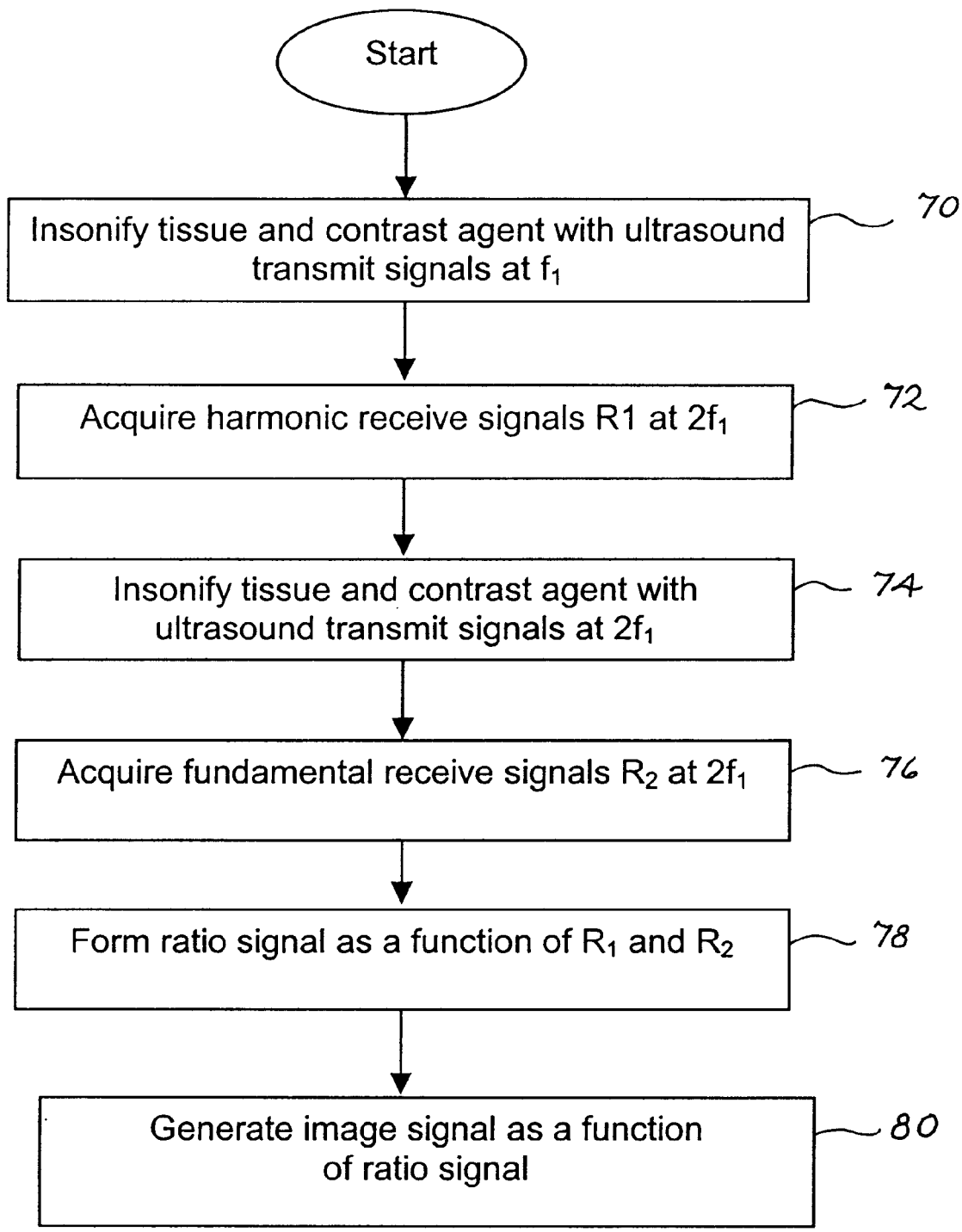
FIG. 5 in a flow chart is a second preferred embodiment of this invention.

FIG. 5 relates to another embodiment of this invention, which can be implemented using a modified version of the system 10 of FIG. 2. In this modified version the transmitter is of the type capable of transmitting pulses at two different transmit center frequencies $f_1$ and $f_2$ on successive firing events. For example, $f_1$ can be equal to the fundamental frequency f described above, and $f_2$ can be equal to the harmonic frequency 2f described above. The other modification to the system 10 is that the ratio former 26 is designed to take a ratio of receive signals from two separate firing events filtered by the filter 24 at 2f. This can be accomplished in any suitable way, as for example by providing a buffer in the ratio former.

Returning to FIG. 5, in step 70 tissue and contrast agent are insonified with ultrasonic transmit signals centered at frequency $f_1$. In step 72 harmonic receive signals R1 are acquired in response to the transmit event of step 70. These harmonic receive signals R1 emphasize harmonic components in a bandpass centered at $2f_1$, as passed by the filter 24 of FIG. 2. In step 74 the tissue and contrast agent are insonified with ultrasound transmit signals in a second transmit event centered at ultrasonic frequency $2f_1$. In step 76 fundamental receive signals R2 are acquired from the second transmit event of step 74. These fundamental receive signals R2 emphasize the same frequency band as that of the receive signals R1, namely $2f_1$. In step 78 a ratio signal is formed as a function of R1 and R2, and in step 80 an image signal is generated as a function of the ratio signal of step 78. The formation of the ratio signal in step 78 and the generation of the image signal in step 80 can employ any of the techniques described elsewhere in this specification.

The method of FIG. 5 uses a ratio of receive signals in the same bandpass acquired in response to two separate transmit events. These two separate transmit events are centered at the fundamental transmit frequency $f_1$ and the second harmonic of this frequency $2f_1$, respectively. The embodiment of FIG. 5 is based on the recognition that the second harmonic response of tissue differs in strength from the second harmonic response of contrast agent, and that the ratio signal of FIG. 5 thereby provides an indication of the presence or absence of contrast agent.

Of course, many modifications and alterations can be made to the preferred embodiments described above. For example, any suitable technology can be used for the transmitter 12 and the receiver 18, including both analog and digital systems. Similarly, any suitable transducer probe 16 can be used, including phased arrays, steered transducers, 1-, 1.5- and 2-dimensional arrays, and flat as well as curved arrays.

The filters 22, 24 can be implemented as desired. For example, the filter 22 can be a lowpass filter and the filter 24 can be a highpass filter, both of which can be considered examples of bandpass filters. Both digital and analog filtering techniques can be used. Demodulation techniques can be used to achieve desired filtering, and if desired the filters 22, 24 can be placed upstream of the receive beamformer in the signal path.

Any suitable detector and integrator can be used in the ratio former. For example, the ratio former 26 can be implemented with a dividing circuit if the detectors 28, 30 are linear detectors as opposed to log detectors. Various elements, including the filters and the integrator for example, can be time-shared between the two processing channels.

The image signal generator 38 does not in all embodiments include a lookup table. Rather, the image signal can be modulated as a linear function of the ratio signal and one of the receive signals, or the ratio signal can be thresholded or applied to an analog or digital function generating circuit. As another alternative, the image signal generator can generate the image signal as a function only of the ratio signal, and not use the ratio signal to modulate another receive signal. Also, the ratio signal can be used as an input to a color image, and the resulting color signal can be displayed either alone or overlaid on a gray-scale image. As before, either analog or digital techniques can be used.

The image processor 46 and the display 48 can take any suitable form, and many variants are known to those skilled in the art. For example, the image processor can include a B-mode processor and/or an M-mode processor. The ratio signal may be displayed as an M-mode strip, either in an overlay mode or by itself. In the overlay mode the ratio signal can be mixed with underlying image data.

Using Parseval's theorem, it can be shown that signal processing can be performed in the time domain instead of the frequency domain to achieve results similar to those described above. The method described above compares the energy of the backscattered signal in two different frequency bands. Ideally, the detectors are of the type that perform a squaring operation. In the frequency domain, the integration frequency range is determined by the signal bandwidth in the fundamental and harmonic frequency bandpass. As another alternative, the filters can be placed before the beamformer when signal processing is performed in the frequency domain.

The system and method described above provide the advantage of improved differentiation of contrast agent from tissue. Because of nonlinear propagation, the presence of signal at the second harmonic frequency does not uniquely identify the presence of contrast and therefore tissue with strong linear scattering can appear brighter in a harmonic image than contrast agent. By modifying the gain based on additional frequency components, the brightness of strong linear scatterers can be reduced and the differentiation of contrast agent from tissue can be improved.

In addition to being beneficial in single pulse harmonic imaging, differential sub-band techniques can be applied to other techniques developed for contrast agent imaging. Specifically, the method described above can be used to improve color Doppler imaging, destruction-based imaging techniques, and pulse inversion imaging techniques. With all these techniques, processing information from several bands simultaneously can provide additional information about the character of the scatterers involved that improves the ability to discriminate between contrast agent and tissue.

The methods described above can be used in conjunction with two-pulse techniques, Doppler techniques, or other harmonic image processing techniques to enhance these methods.

The image formed using the methods described above can be constructed over multiple frames including one or more frames designed to destroy contrast agent. The rate at which the ratio of the harmonic over the fundamental signal varies is measured in order to establish a perfusion rate.

As used herein, the term "harmonic" is intended broadly to encompass both harmonics and subharmonics. The term "signal" is intended broadly to encompass both analog and digital signals.

As used herein, one signal is said to vary as a function of another whether or not the first signal also varies as a function of additional, unnamed parameters. Thus, an image signal is said to vary as a function of a gain signal, whether or not the image signal also varies as a function of the fundamental or harmonic receive signals F, H. Also, the term "function of" is intended broadly to encompass systems that include integrators, as well as systems that do not. Thus, a ratio signal is said to vary as a function of a ratio of fundamental and harmonic receive signal, whether or not integrators are placed in the signal path.

The term "fundamental receive signal" is intended to encompass a receive signal that has been filtered or demodulated to emphasize the fundamental component of the receive signal, recognizing that a fundamental receive signal will have a bandwidth that extends to some extent beyond the fundamental frequency itself. Similarly, the term "harmonic receive signal" is intended to refer to a receive signal that has been filtered or demodulated to emphasize harmonic spectral components, and a harmonic receive signal will also have a bandwidth that extends around the specific harmonic frequency.

The term "ratio" is intended broadly both to encompass the quotient of two linear signals and the difference of two logarithmic signals. The term "ratio" is also intended to encompass regularized ratios. For example, one type of regularized ratio that is commonly used to reduce artifacts adds a non-zero constant to the denominator of the ratio in order to prevent the denominator from ever being set equal to zero. In one example, the ratio F/H can be set equal to F/(H+X), where X is a non-zero constant.

The foregoing detailed description has described only a few of the many forms that this invention can take. For this reason, this detailed description is intended by way of illustration and not by way of limitation. It is only the following claims, including all equivalents, that are intended to define the scope of this invention.

What is claimed is:

1. A medical diagnostic ultrasound imaging method comprising:
   (a) insonifying a tissue containing a contrast agent with ultrasonic transmit signals;
   (b) acquiring backscattered ultrasonic first receive signals in a first bandpass;
   (c) acquiring backscattered ultrasonic second receive signals in a second bandpass;
   (d) forming a gain signal as a function of the first and second receive signals; and
   (e) applying the gain signal to backscattered ultrasonic receive signals.

2. A medical diagnostic ultrasound image processing method responsive to a first receive signal and a second receive signal, said first and second receive signals characterized by separate respective first and second bandpasses, said method comprising:
   forming a gain signal as a function of the first and second receive signals; and
   applying the gain signal to backscattered ultrasonic receive signals.

3. The method of claim 1 or 2, wherein the gain signal forming act comprises
   forming a ratio signal as a function of the first and second receive signals; and
   applying the ratio signal as an input to a lookup table that generates the gain signal in response thereto.

4. The method of claim 3, wherein the gain signal applying act comprises
   applying the gain signal and at least one of the first and second receive signals to a multiplier that generates an image signal in response thereto.

5. The method of claim 3 wherein the lookup table generates the gain signal as an non-linear function of the ratio signal.

6. The method of claim 1 or 2, wherein the gain signal forming act step comprises
   detecting and log compressing the first receive signal;
   integrating the detected and log compressed first receive signal;
   detecting and log compressing the second receive signal;
   integrating the detected and log compressed second receive signal; and
   applying the integrated, detected, log compressed first receive signal and the integrated, detected, log compressed second receive signal to a ratio former which generates a ratio signal.

7. The method of claim 1 wherein (b) comprises applying echo signals from a first transmit event to a first filter, and wherein (c) comprises applying echo signals from the first transmit event to a second filter.

8. The method of claim 7 wherein the transmit signals of the first transmit event are characterized by a fundamental frequency, wherein the first filter selectively passes fundamental components of the echo signals, and wherein the second filter selectively passes harmonic components of the echo signals.

9. A medical diagnostic ultrasound imaging method comprising:
   (a) insonifying a tissue containing a contrast agent with ultrasonic transmit signals;
   (b) acquiring backscattered ultrasonic first receive signals in a first bandpass;
   (c) acquiring backscattered ultrasonic second receive signals in a second bandpass;
   (d) forming a ratio signal as a function of the first and second receive signals; and
   (e) generating an image signal as a function of the ratio signal;
   wherein (a) comprises
      (a1) insonifying the tissue containing the contrast agent with a first transmit event characterized by ultrasonic transmit signals having a first center frequency $f_1$; and
      (a2) insonifying the tissue containing the contrast agent with a second transmit event characterized by ultrasonic transmit signals having a second center frequency $f_2$.

10. The method of claim 9 wherein the first and second bandpasses are characterized by first and second filter center frequencies, respectively, wherein the first and second filter center frequencies are both substantially equal to $f_2$, and wherein $f_2$ is about twice $f_1$.

11. The method of claim 9 wherein the first and second bandpasses are characterized by substantially equal filter center frequencies.

12. The method of claim 1 wherein (e) generates an image signal selected from the group consisting of B-mode, M-mode, color flow image signals, and combinations thereof.

13. A medical diagnostic ultrasound imaging system comprising:
   means for insonifying a tissue containing a contrast agent with ultrasonic transmit signals;
   first means for acquiring backscattered ultrasonic first receive signals in a first bandpass;
   second means for acquiring backscattered ultrasonic second receive signals in a second bandpass;
   means for forming a gain signal as a function of the first and second receive signals; and
   means for applying the gain signal to backscattered ultrasonic receive signals.

14. The invention of claim 13, wherein the gain signal forming means comprises
   a ratio former responsive to the first and second receive signals; and
   a lookup table responsive to the ratio former to generate the gain signal.

15. The invention of claim 14, wherein the gain signal applying means comprises a multiplier responsive to the gain signal and to at least one of the first and second receive signals to generate an image signal.

16. The invention of claim 13, wherein the gain signal forming means comprises:
   a first log detector responsive to the first receive signal;
   a first integrator responsive to the first detector;
   a second log detector responsive to the second receive signal;
   a second integrator responsive to the second detector; and
   an element responsive to the first and second integrators to generate a ratio signal.

17. The invention of claim 13, wherein the first and second means comprise first and second filters, respectively, and wherein the first and second means are operative to acquire the first and second receive beams, respectively, from a common transmit event.

18. The invention of claim 17, wherein the transmit signals are characterized by a fundamental frequency, wherein the first bandpass emphasizes fundamental components of the first receive signals, and wherein the second bandpass emphasizes harmonic components of the second receive signals.

19. A medical diagnostic ultrasound imaging system comprising:

means for insonifying a tissue containing a contrast agent with ultrasonic transmit signals;

first means for acquiring backscattered ultrasonic first receive signals in a first bandpass;

second means for acquiring backscattered ultrasonic second receive signals in a second bandpass;

means for forming a ratio signal as a function of the first and second receive signals; and means for generating an image signal as a function of the ratio signal;

wherein the insonifying means is operative to insonify the tissue containing the contrast agent with (1) first transmit signals from a first transmit event having a first center frequency $f_1$ and (2) second transmit signals from a second transmit event having a second center frequency $f_2$.

20. The invention of claim 19, wherein the first and second bandpasses both selectively pass receive signals at the second center frequency $f_2$, and wherein $f_2$ is about twice $f_1$.

21. The invention of claim 19, wherein the first and second bandpasses are characterized by substantially equal center frequencies.

22. The invention of claim 13 wherein the gain signal applying means generates an image signal selected from the group consisting of B-mode, M-mode, color flow image signals and combination thereof.

23. A medical diagnostic ultrasound image processor responsive to a first receive signal and a second receive signal, said first and second receive signals characterized by separate respective first and second bandpasses, said image processor comprising:

a gain signal generator operative to form a gain signal as a function of the first receive signal and the second receive signal; and an image signal generator operative to apply the gain signal to backscattered ultrasonic receive signals.

24. The invention of claim 23, wherein the gain signal generator comprises:

a ratio former operative to form a ratio signal as a function of the first and second receive signals; and a lookup table responsive to the ratio signal to generate the gain signal.

25. The invention of claim 24, wherein the image signal generator further comprises:

a multiplier responsive to the gain signal and to at least one of the first and second receive signals to generate an image signal.

26. The invention of claim 14 or 24 wherein the lookup table generates the gain signal as an non-linear function of the ratio signal.

27. The invention of claim 23, wherein the gain signal generator comprises:

a first log detector responsive to the first receive signal;

a first integrator responsive to the first detector;

a second log detector responsive to the second receive signal;

a second integrator responsive to the second detector; and an element responsive to the first and second integrators to generate a ratio signal.

28. The invention of claim 23, wherein the first and second bandpasses are centered at respective center frequencies $f_1$ and $f_2$, and wherein $f_2$ is substantially equal to two times $f_1$.

29. A medical diagnostic ultrasound image processor responsive to a first receive signal and a second receive signal, said first and second receive signals characterized by separate respective first and second bandpasses, said image processor comprising:

a ratio former operative to form a ratio signal as a function of the first receive signal and the second receive signal; and an image signal generator operative to generate an image signal as a function of the ratio signal;

wherein the first and second bandpasses are centered at substantially equal center frequencies, and wherein the first and second receive signals are associated with separate respective transmit events.

30. The invention of claim 23 wherein the image signal generator generates an image signal selected from the group consisting of B-mode, M-mode, color flow image signals and combination thereof.

31. The invention of claim 13 wherein the gain signal applying means applies the gain signal to fundamental ultrasonic receive signals prior to display.

32. The method of claim 1 wherein (e) comprises applying the gain signal to fundamental ultrasonic receive signals prior to display.

\* \* \* \* \*